(12) United States Patent
Kamihara

(10) Patent No.: US 7,557,927 B2
(45) Date of Patent: Jul. 7, 2009

(54) OPTICAL APPARATUS FOR CAPTURING SPECTRAL IMAGE

(75) Inventor: Yasuhiro Kamihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 241 days.

(21) Appl. No.: 11/803,537

(22) Filed: May 15, 2007

(65) Prior Publication Data

US 2007/0268493 A1 Nov. 22, 2007

(30) Foreign Application Priority Data

May 22, 2006 (JP) .............................. 2006-141382

(51) Int. Cl.
*G01B 9/02* (2006.01)
*G01J 3/45* (2006.01)
(52) U.S. Cl. ....................... 356/456; 356/454
(58) Field of Classification Search ................. 356/451, 356/454, 456, 480, 519
See application file for complete search history.

(56) References Cited

U.S. PATENT DOCUMENTS 4,859,060 A * 8/1989 Katagiri et al. ............. 356/454
5,818,586 A * 10/1998 Lehto et al. ................. 356/454
6,344,647 B1 * 2/2002 Jourdain et al. ........ 250/339.07
6,747,742 B1 * 6/2004 Verma ........................ 356/454
6,985,233 B2 * 1/2006 Tuschel et al. ............. 356/454
7,061,618 B2 * 6/2006 Atia et al. ................... 356/454

FOREIGN PATENT DOCUMENTS

JP 2802061 7/1998

OTHER PUBLICATIONS

Abstract of Japanese Patent Application Publication No. 63-271308 dated Sep. 11, 1988.

* cited by examiner

*Primary Examiner*—Michael A Lyons
(74) *Attorney, Agent, or Firm*—Scully, Scott, Murphy & Presser, P.C.

(57) ABSTRACT

An optical apparatus for capturing spectral images includes a variable spectroscopy device having first and second optical members that face each other and have a space therebetween, the spectral characteristics of the variable spectroscopy device being changed in accordance with changes in the relative positions of these optical members; a frame member that fixes the first optical member in place; a driving section disposed between the frame member and the second optical member, and transferring the second optical member with respect to the frame member in accordance with driving signals input to the driving section; and an optical element that deflects or disperses light beams passing through the variable spectroscopy device or a photoelectric conversion element that conducts photoelectric conversion. The optical element or the photoelectric conversion element is supported by the frame member.

23 Claims, 13 Drawing Sheets

OPTICAL APPARATUS FOR CAPTURING SPECTRAL IMAGE

BACKGROUND OF THE INVENTION

1. Field of the Invention

The present invention relates to optical apparatuses for capturing spectral images, and in particular, relates to a technology for acquiring spectral information on living bodies and the like using etalon elements.

This application is based on Japanese Patent Application No. 2006-141382, the content of which is incorporated herein by reference.

2. Description of Related Art

In a technology (for example, see the specification of Japanese Patent No. 2802061), wavelength characteristics of observation light or illumination light can be changed by using an etalon element capable of changing gaps between a plurality of optical members using driving means formed of piezoelectric elements and disposed in at least one of an imaging optical system and an illumination optical system disposed at the leading end of an endoscope.

Spectral information on living bodies and the like can be acquired using this technology disclosed in the specification of Japanese Patent No. 2802061.

The etalon element disclosed in the specification of Japanese Patent No. 2802061 includes the driving means formed of the piezoelectric elements disposed between two or more optical members. Since the etalon element changes the transmission characteristics thereof using an optical interference effect, it is necessary to reduce the gaps between adjacent pairs of the optical members to approximately the coherence length of light beams or less, and at the same time, the driving means for transferring the optical members requires high driving resolution.

In order to efficiently adjust the gaps between adjacent pairs of the optical members to the coherence length of the light beams or less, moving distances of driving sections need to be increased. However, it is difficult to increase the moving distances of the driving sections in the structure disclosed in the specification of Japanese Patent No. 2802061 having the driving means disposed between two or more optical members.

BRIEF SUMMARY OF THE INVENTION

The present invention provides the following solutions.

According to an aspect of the present invention, an optical apparatus for capturing spectral images includes a variable spectroscopy device having first and second optical members that face each other and have a space therebetween, the spectral characteristics of the variable spectroscopy device being changed in accordance with changes in the relative positions of these optical members; a frame member that fixes the first optical member in place; a driving section disposed between the frame member and the second optical member, and transferring the second optical member with respect to the frame member in accordance with driving signals input to the driving section; an optical element that deflects or disperses light beams passing through the variable spectroscopy device; or a photoelectric conversion element that conducts photoelectric conversion. The optical element or the photoelectric conversion element is supported by the frame member.

In the above-described aspect of the present invention, the optical apparatus can be used for capturing spectral images of body tissue, or can be used for capturing spectral images of tissue inside a cavity of a living body.

Moreover, at least part of the driving section, and part of the optical element or part of the photoelectric conversion element are preferably overlapped with each other in a direction of the optical axis of the optical apparatus.

Moreover, in the above-described aspect, the optical element can be a lens or a filter.

Moreover, the photoelectric conversion element can convert incident light into electrical energy, or convert input electrical energy into light.

Moreover, in the above-described aspect, the driving section can be arranged to be on both sides of the optical axis of the optical apparatus.

Furthermore, the driving section can transfer the second optical member in the direction of the optical axis of the optical apparatus.

Moreover, in the above-described aspect, the first optical member can be disposed between the second optical member and a position where the driving section is supported by the frame member.

Moreover, the second optical member can be disposed between the first optical member and a position where the driving section is supported by the frame member.

Moreover, in the above-described aspect, the photoelectric conversion element can be a light-receiving element; and the optical element can focus light beams passing through the variable spectroscopy device on the light-receiving element.

Moreover, the photoelectric conversion element can be a light source; and the optical element can project light beams passing through the variable spectroscopy device onto an observation target.

Moreover, in the above-described aspect, the light source can be a surface illuminant.

Moreover, when the optical element focuses the light beams passing through the variable spectroscopy device onto the light-receiving element as described above, the light beams passing through the variable spectroscopy device can be non-collimated beams.

Moreover, in the above-described structure, the optical element can have a refractive power to the light beams passing through the variable spectroscopy device.

Moreover, in the above-described aspect, the frame member can be cylindrical; and the variable spectroscopy device, the driving section, and the optical element or the photoelectric conversion element can be disposed inside the frame member.

Moreover, in the above-described aspect, the driving section can change the size of the space between the first optical member and the second optical member.

Moreover, in the above-described structure, the optical apparatus can further include a gap-detecting section that detects the size of the space between the first optical member and the second optical member.

DETAILED DESCRIPTION OF THE INVENTION

An optical apparatus 1 for capturing spectral images according to a first embodiment of the present invention will now be described with reference to FIGS. 1 to 3.

Figure 1:
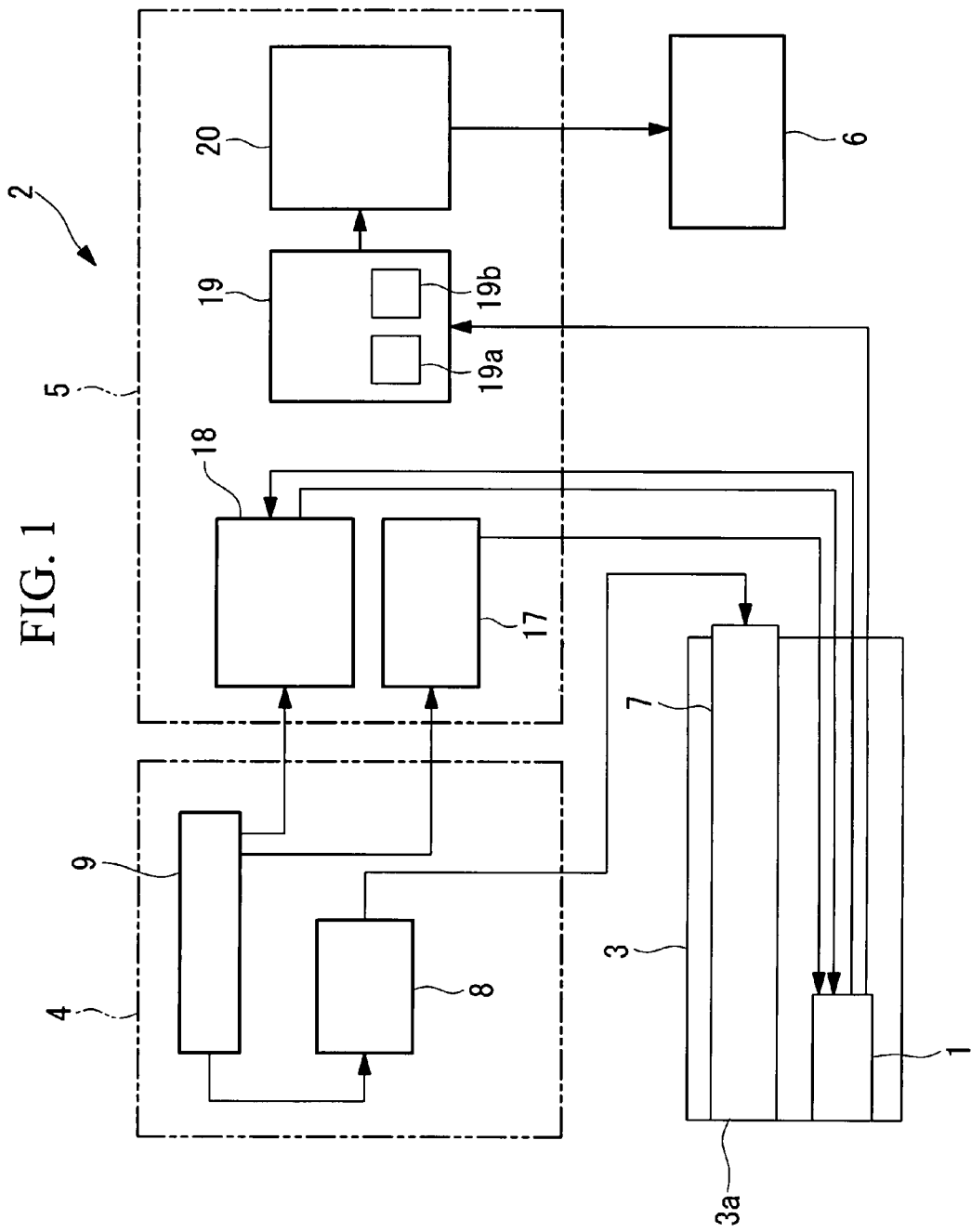
FIG. 1 is a block diagram illustrating the structure of an endoscope system including an image pickup unit according to a first embodiment of the present invention.

The optical apparatus (hereinafter referred to as "image pickup unit") 1 according to this embodiment is installed in an endoscope system 2 as shown in FIG. 1.

As shown in FIG. 1, the endoscope system 2 includes an insertion section 3 inserted into a cavity of a living body, the image pickup unit 1 disposed inside the insertion section 3, a light source unit (light source) 4 that emits a plurality of types of light beams, a control unit (control section) 5 that controls the image pickup unit 1 and the light source unit 4, and a display unit (display section) 6 that displays images captured by the image pickup unit 1.

The insertion section 3 has a narrow shape whose outer dimensions are extremely small so as to allow insertion into a cavity of a living body, and includes the image pickup unit 1 and a light guide 7 that transmits light beams emitted from the light source unit 4 to the leading end 3a of the insertion section 3.

The light source unit 4 includes a light source 8 that emits illumination beams for illuminating an observation target in the body cavity and a light source control circuit 9 that controls the light source 8.

The light source 8 includes, for example, a combination of a xenon lamp and a band-pass filter (not shown), and the band-pass filter has a 50% passband ranging from 430 to 700 nm. That is, the light source 8 generates illumination beams in a wavelength band from 430 to 700 nm.

Figure 2:
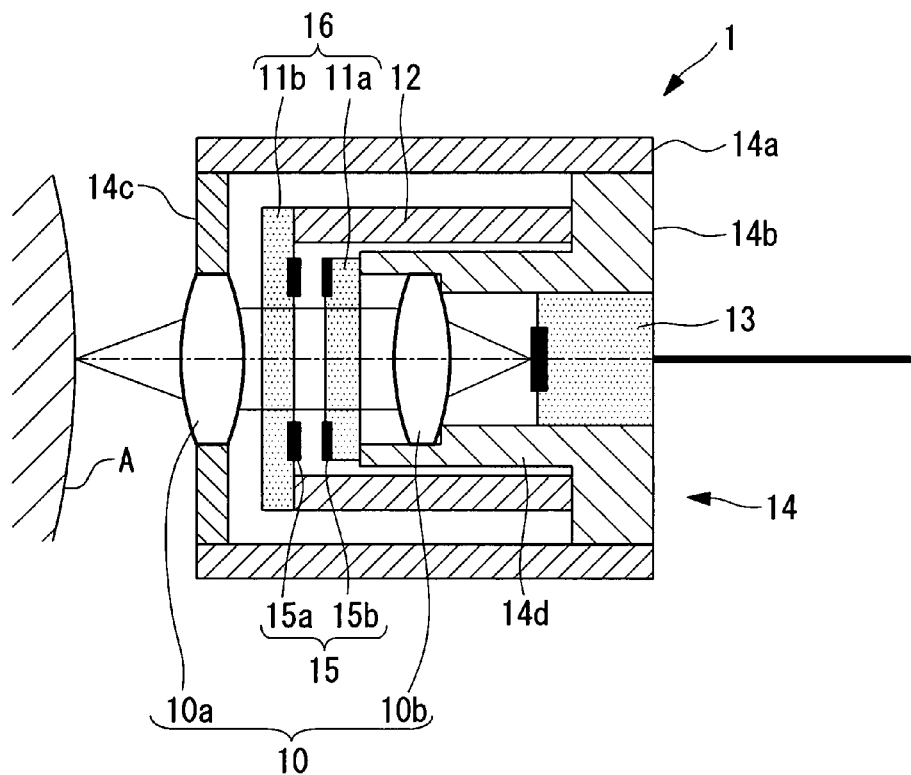
FIG. 2 is a schematic longitudinal sectional view illustrating the image pickup unit according to the first embodiment of the present invention.

As shown in FIG. 2, the image pickup unit 1 according to this embodiment includes an imaging optical system 10 that collects light reflected from an observation target A, first and second optical members 11a and 11b, respectively, disposed so as to have a space therebetween, the collected light transmitting through the optical members 11a and 11b, an actuator (driving section) 12 operated in accordance with an operation of the control unit 5, an image-pickup element (photoelectric conversion element) 13 that captures light beams collected by the imaging optical system 10 and converts the light beams into electrical signals, and a frame member 14 that supports these components.

The imaging optical system 10 includes a first lens (optical element) 10a and a second lens (optical element) 10b.

The opposing surfaces of the optical members 11a and 11b in a range of an effective optical diameter are covered with a reflective coating (not shown). The reflective coating is formed of, for example, a metallic film, a dielectric multilayer film, and the like. The gap between the surfaces of the optical members 11a and 11b is extremely small, and is, for example, on the order of microns.

Moreover, ring-shaped sensor electrodes 15a and 15b constituting a capacitive sensor (gap-detecting section) 15 are disposed on the optical members 11a and 11b, respectively, outside the reflective coating, applied to the optical members 11a and 11b in the range of the effective optical diameter, in radial directions. The sensor electrodes 15a and 15b are formed of, for example, metallic films. Thus, the capacitive sensor 15 can detect the size of the gap between the sensor electrodes 15a and 15b on the basis of a capacitance that is changed in accordance with the gap between the sensor electrodes 15a and 15b.

The actuator 12 is formed of, for example, a cylindrical piezoelectric element. When a driving signal is input to the actuator 12, the length of the actuator 12 is changed in accordance with the driving signal. The wavelength band of light beams transmitting through the gap can be changed by changing the size of the gap between the optical members 11a and 11b in accordance with the operation of the actuator 12.

The frame member 14 includes an outer cylinder 14a, and first and second supporting members 14b and 14c, respectively, fixed to the inner surface of the outer cylinder 14a.

One end of the actuator 12 is fixed to the first supporting member 14b, and the other end is fixed to the second optical member 11b. The first supporting member 14b includes a cylindrical portion 14d formed at the central portion of the first supporting member 14b in radial directions thereof and extending inside the actuator 12. The first optical member 11a is fixed to the end of the cylindrical portion 14d.

Moreover, the second lens 10b and the image-pickup element 13 are disposed inside the cylindrical portion 14d in radial directions of the cylindrical portion 14d so as to have a space therebetween in the axial direction of the actuator 12. Thus, the first optical member 11a, the second lens 10b, the image-pickup element 13, and the actuator 12 including these components are coaxially disposed.

Moreover, the second supporting member 14c supports the first lens 10a disposed on a side of the optical members 11a and 11b opposite that on which the second lens 10b lies. The outer cylinder 14a, the first supporting member 14b, and the second supporting member 14c constituting the frame member 14, the lenses 10a and 10b, the optical members 11a and 11b, the image-pickup element 13, and the actuator 12 are fixed to each other using, for example, an adhesive.

The optical members 11a and 11b constitute a variable spectroscopy device 16 capable of adjusting the transmittance characteristics thereof in high resolution.

Figure 3:
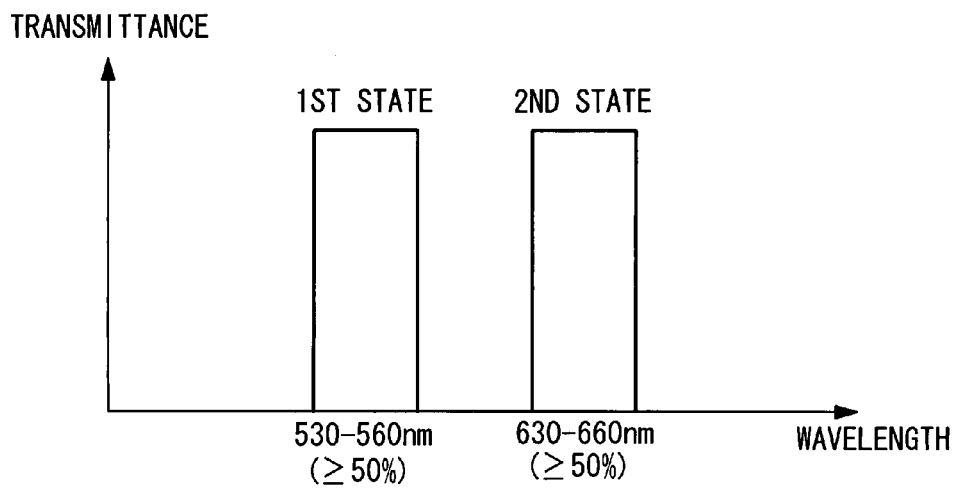
FIG. 3 illustrates transmittance characteristics of a variable spectroscopy device constituting the image pickup unit shown in FIG. 2.

As shown in FIG. 3, the variable spectroscopy device 16 is switched between two states each having a specific wavelength band in accordance with control signals sent from the control unit 5. Feedback control of the control signals on the basis of signals from the capacitive sensor 15 can improve the control accuracy.

Light beams having wavelengths ranging from 530 to 560 nm (visible green light) can transmit through the variable spectroscopy device 16 in the first state (the transmission wavelength band is defined by wavelengths of light beams, 50% of which can transmit through the variable spectroscopy device 16).

Light beams having wavelengths ranging from 630 to 660 nm (visible red light) can transmit through the variable spectroscopy device 16 in the second state.

As shown in FIG. 1, the control unit 5 includes a second control circuit 17 that drives the image-pickup device 13, a third control circuit 18 that controls the variable spectroscopy device 16, a frame memory 19 that retains image information acquired by the image-pickup element 13, and an image-processing circuit 20 that processes the image information retained in the frame memory 19 and outputs the information to the display unit 6.

The second control circuit 17 and the third control circuit 18 are connected to the light source control circuit 9 so as to control the image-pickup element 13 and the variable spectroscopy device 16, respectively.

More specifically, when the third control circuit 18 drives the variable spectroscopy device 16 to be switched to the first state, the second control circuit 17 drives the image-pickup element 13 to output the image information to a first frame-memory segment 19a. Moreover, when the third control circuit 18 drives the variable spectroscopy device 16 to be switched to the second state, the second control circuit 17 drives the image-pickup element 13 to output the image information to a second frame-memory segment 19b.

Moreover, the image-processing circuit 20 receives, for example, image information on reflected beams in the green range from the first frame-memory segment 19a, and outputs the information to a first channel of the display unit 6. Alternatively, the image-processing circuit 20 receives image information on reflected beams in the red range from the second frame-memory segment 19b, and outputs the information to a second channel of the display unit 6.

Operations of the endoscope system 2 including the above-described image pickup unit 1 according to this embodiment will now be described.

In order to capture images of the observation target A in a cavity of a living body using the endoscope system 2 including the image pickup unit 1 according to this embodiment, the insertion section 3 is inserted into the cavity, and is disposed such that the leading end 3a of the insertion section 3 faces the observation target A in the cavity. In this arrangement, the light source unit 4 and the control unit 5 are operated such that the light source 8 emits illumination beams in accordance with the operation of the light source control circuit 9.

The illumination beams generated at the light source 8 of the light source unit 4 are transmitted to the leading end 3a of the insertion section 3 via the light guide 7, and emitted from the leading end 3a of the insertion section 3 to the observation target A.

The illumination beams are reflected from the surface of the observation target A, and collimated by the first lens 10a so as to become substantially parallel to each other. Subsequently, the illumination beams transmit through the variable spectroscopy device 16, and are focused on the image-pickup element 13 by the second lens 10b. As a result, image information on the reflected beams is acquired.

When image information on the reflected beams in the green range is acquired, the variable spectroscopy device 16 is switched to the first state by the third control circuit 18. As a result, the wavelength band of the reflected beams that reach the image-pickup element 13 can be limited from 530 to 560 nm. The acquired image information on the reflected beams is retained in the first frame-memory segment 19a, output by the image-processing circuit 20 to the first channel of the display unit 6, and displayed on the display unit 6.

When image information on the reflected beams in the red range is acquired, the variable spectroscopy device 16 is switched to the second state by the third control circuit 18. As a result, the wavelength band of the reflected beams that reach the image-pickup element 13 can be limited from 630 to 660 nm. The acquired image information on the reflected beams is retained in the second frame-memory segment 19b, output by the image-processing circuit 20 to the second channel of the display unit 6, and displayed on the display unit 6.

As described above, in accordance with the endoscope system 2 including the image pickup unit 1 according to this embodiment, image information on reflected beams in different wavelength bands can be provided for a user.

In this case, in accordance with the image pickup unit 1 according to this embodiment, the first optical member 11a, the second lens 10b, and the image-pickup element 13 are disposed inside the cylindrical actuator 12. Therefore, the total length of the image pickup unit 1 can be reduced while ensuring a sufficient moving distance of the actuator 12 as compared with the known case in which these components are arranged in series. In particular, the length of the leading end, which is an undeformable hard portion in the endoscope system 2, can be advantageously reduced.

Various changes and modifications are applicable to the structure of the image pickup unit 1 according to this embodiment.

Figure 4:
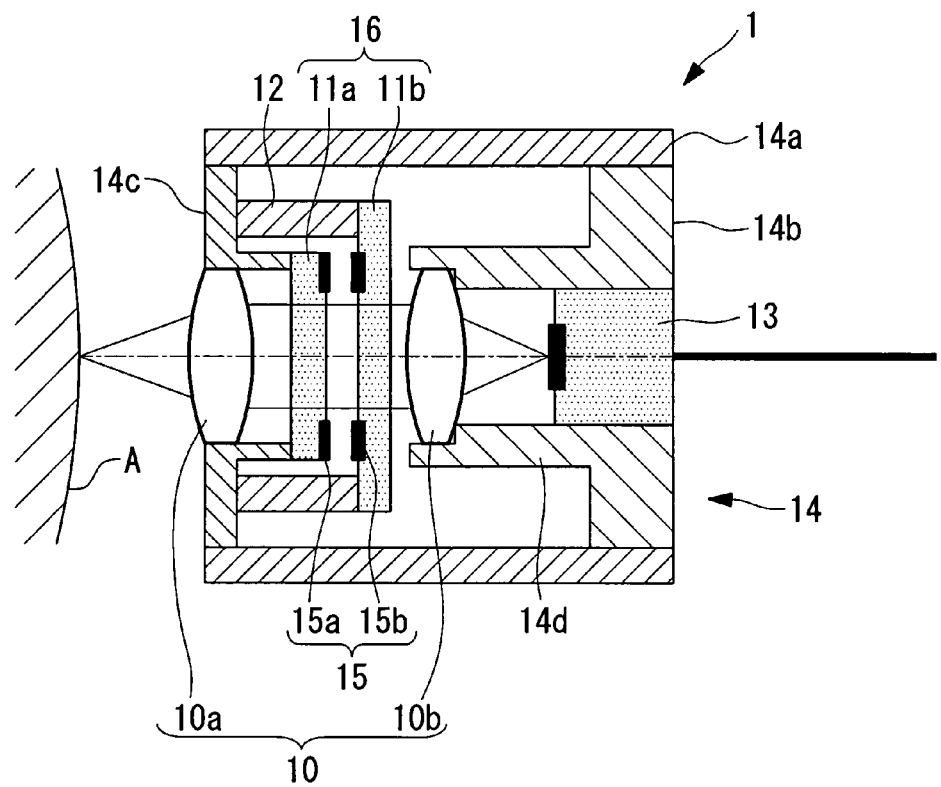
FIG. 4 is a schematic longitudinal sectional view illustrating a modification of the image pickup unit shown in FIG. 2.

For example, the cylindrical actuator 12 is disposed between the first supporting member 14b and the second optical member 11b in this embodiment. Alternatively, as shown in FIG. 4, the actuator 12 can be disposed between the second optical member 11b and the second supporting member 14c, and the first optical member 11a and the first lens 10a can be disposed inside the actuator 12.

As a result, the first lens 10a is disposed inside the actuator 12, thereby reducing the total length of the image pickup unit 1 while ensuring a sufficient moving distance of the actuator 12.

Figure 5:
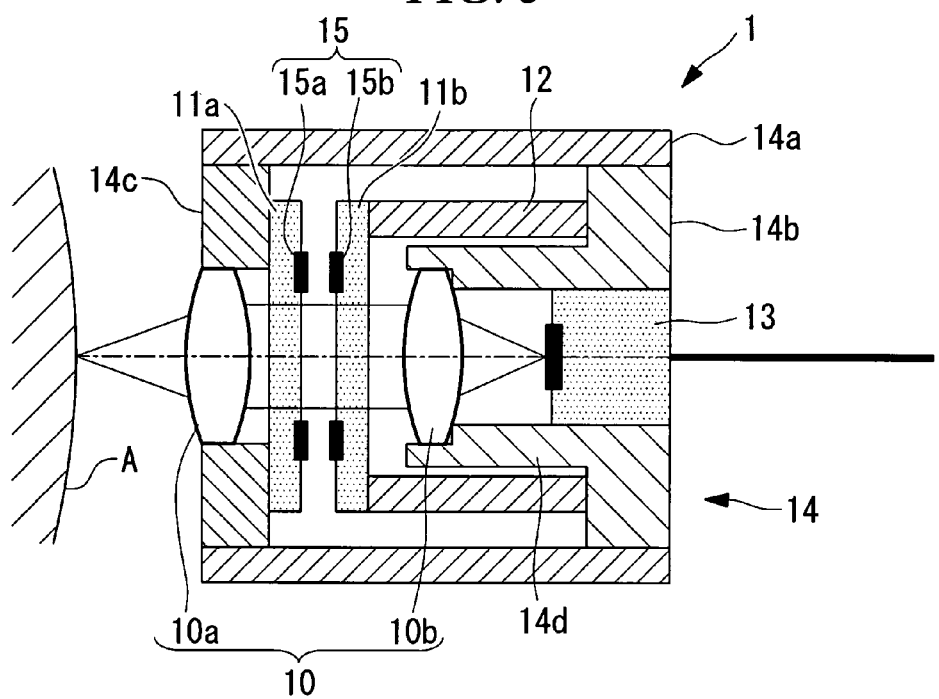
FIG. 5 is a schematic longitudinal sectional view illustrating another modification of the image pickup unit shown in FIG. 2.

Moreover, as shown in FIG. 5, the actuator 12 can be disposed between the second optical member 11b and the first supporting member 14b, and the first optical member 11a can be supported by the second supporting member 14c. As a result, the first optical member 11a, which is required to be accurately arranged, does not need to be nested in the actuator 12. This can simplify the structure, and facilitate the assembly.

Figure 6:
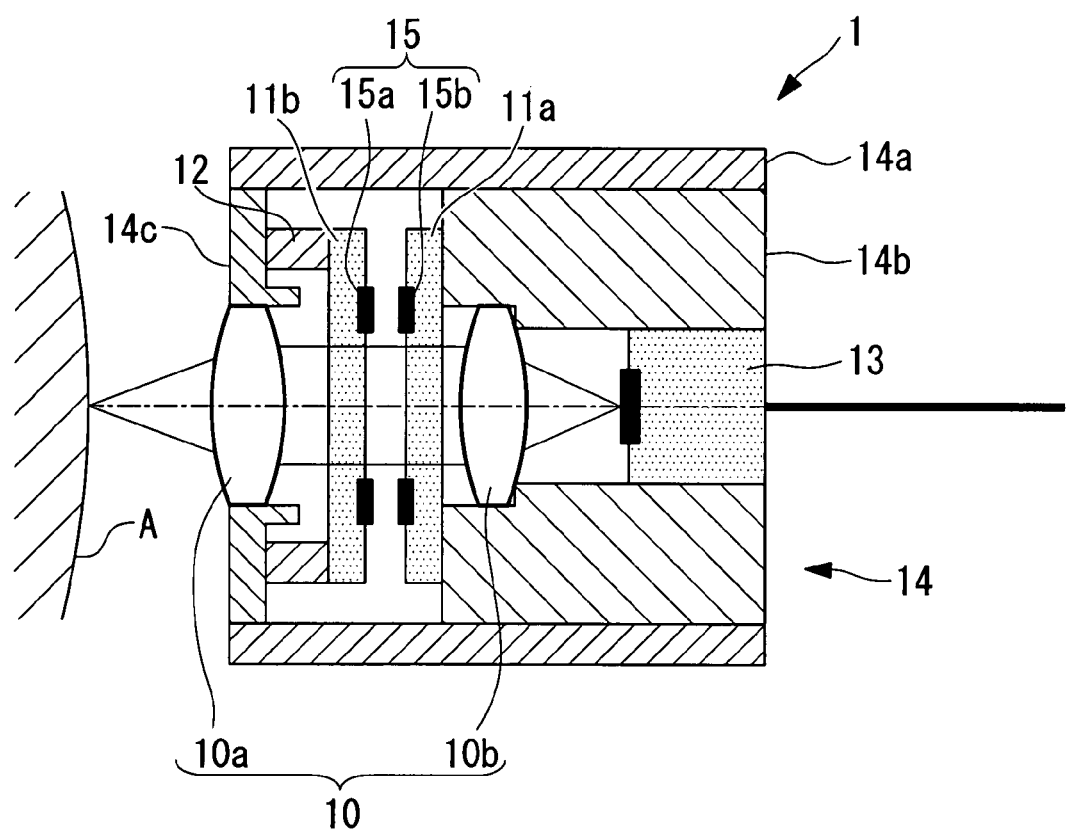
FIG. 6 is a schematic longitudinal sectional view illustrating yet another modification of the image pickup unit shown in FIG. 2.

Furthermore, as shown in FIG. 6, the actuator 12 can be disposed between the second optical member 11b and the second supporting member 14c, and the first optical member 11a can be supported by the first supporting member 14b. As a result, the first lens 10a is disposed inside the actuator 12, thereby reducing the total length of the image pickup unit 1 while ensuring a sufficient moving distance of the actuator 12.

Moreover, a charge-coupled device (CCD), a complementary metal oxide semiconductor (CMOS) device, a photodiode, an electron-multiplying CCD (EMCCD), an electron-bombarded CCD (EBCCD), and the like can be adopted to the image-pickup element 13.

Moreover, the frame member 14 and the actuator 12 can be fixed using other methods, for example, using setscrews or by engagement with each other. Moreover, a magnetostrictive element, for example, can be adopted to the actuator 12 instead of a piezoelectric element. Moreover, the image pickup unit 1 is also applicable to a rigid scope in addition to a flexible scope. Furthermore, the image pickup unit 1 is applicable to an objective lens for observing inside a living body instead of the endoscope system 2.

Next, an image pickup unit 30 according to a second embodiment of the present invention and an endoscope system 31 including the image pickup unit 30 will be described with reference to FIGS. 7 to 9.

In the description of this embodiment, the same reference numerals are used for components common to those in the image pickup unit 1 according to the first embodiment, and the description thereof will be omitted.

Figure 7:
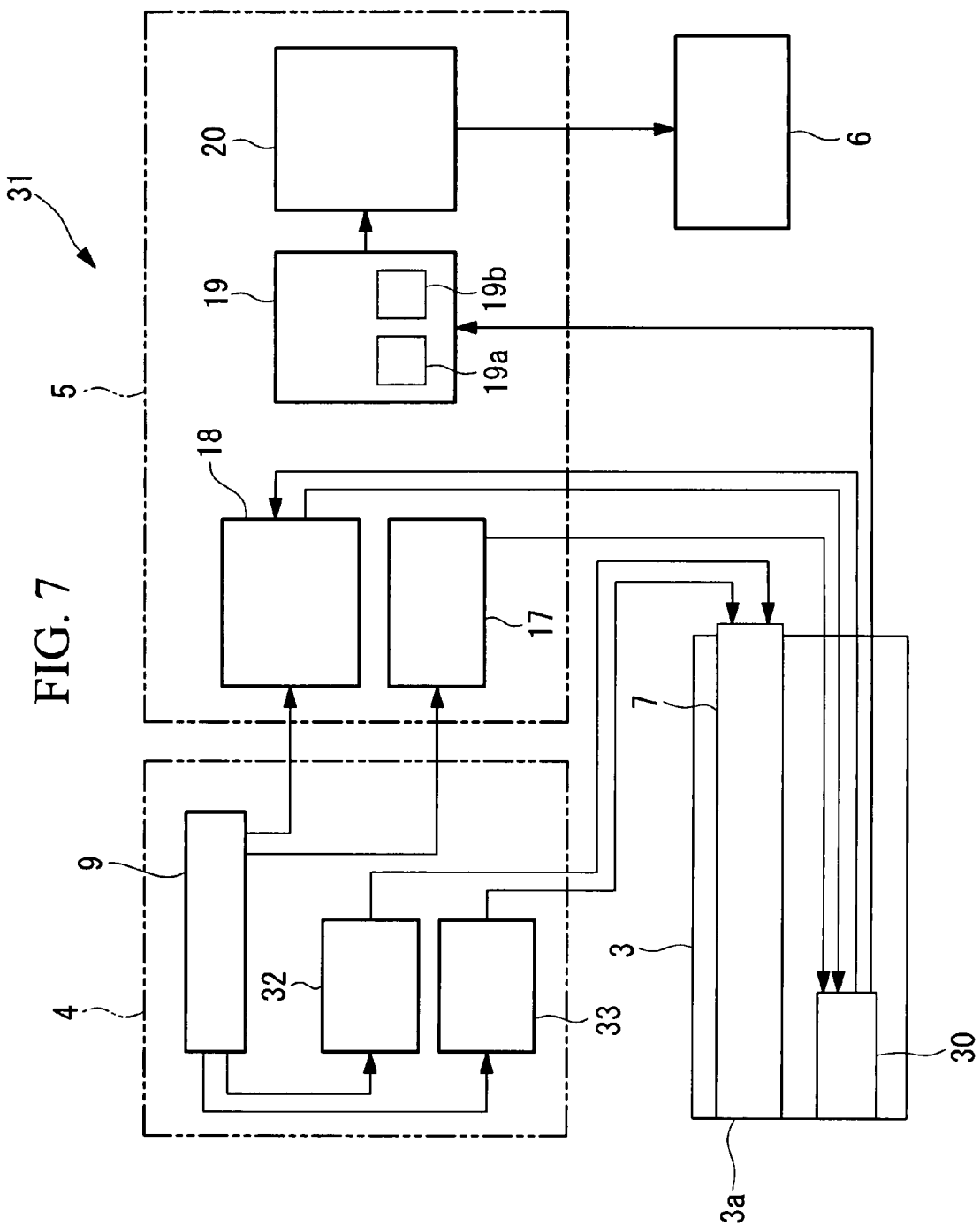
FIG. 7 is a block diagram illustrating the structure of an endoscope system including an image pickup unit according to a second embodiment of the present invention.

As shown in FIG. 7, the endoscope system 31 including the image pickup unit 30 according to this embodiment differs from the endoscope system 2 in the first embodiment in that the endoscope system 31 captures images of fluorescent beams in addition to images of reflected beams. Moreover, wavelength bands of images of reflected beams also differ from those in the first embodiment.

A light source unit 4 includes an illumination light source 32 that emits illumination beams illuminating an observation target in a body cavity and reflected from the observation target, an excitation light source 33 that emits excitation beams emitted to the observation target in the body cavity so as to excite fluorescent materials existing in the observation target to generate fluorescent beams, and a light source control circuit 9 that controls these light sources 32 and 33.

The illumination light source 32 includes, for example, a combination of a xenon lamp and a band-pass filter (not shown), and the band-pass filter has a 50% passband ranging from 430 to 460 nm. That is, the illumination light source 32 generates illumination beams in a wavelength band from 430 to 460 nm.

The excitation light source 33 is, for example, a semiconductor laser that emits excitation beams having a peak wavelength of 660±5 nm. The excitation beams having this wavelength can excite fluorescent agents such as Cy5.5 (registered trademarks of GE Healthcare, Inc. (formerly Amersham Biosciences Corp.)) and Alexa Fluor® 700 (of Molecular Probes, Inc.).

The light source control circuit 9 alternately turns on and off the illumination light source 32 and the excitation light source 33 at timings according to a timing chart (described below).

Figure 8:
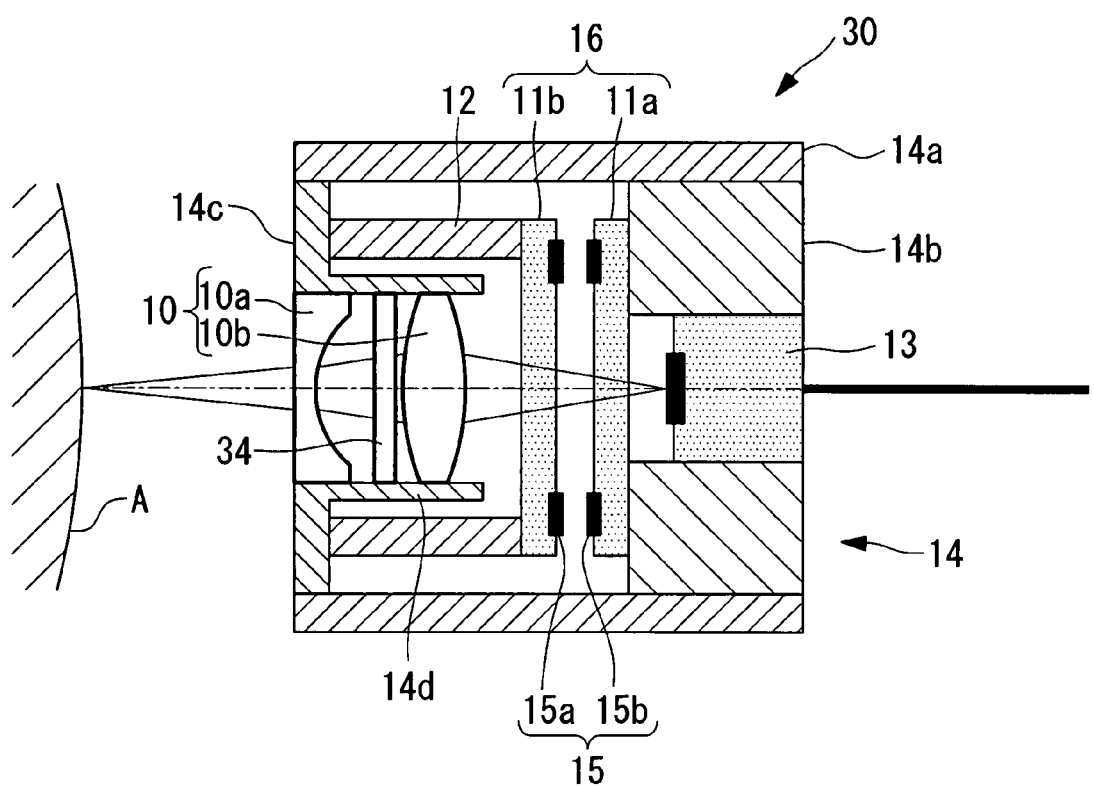
FIG. 8 is a schematic longitudinal sectional view illustrating the image pickup unit according to the second embodiment of the present invention.

As shown in FIG. 8, the image pickup unit 30 includes an imaging optical system 10, including a first lens 10a and a second lens 10b, for collecting light beams reflected from an observation target A, a cut-off filter (optical element; filter) 34 that blocks excitation beams reflected from the observation target A, a variable spectroscopy device (variable spectroscopy section) 16 capable of changing the spectral characteristics thereof in accordance with the operation of a control unit 5, an image-pickup element 13 that captures light beams collected by the imaging optical system 10 and converts the light beams into electrical signals, and a frame member 14 that supports these components.

An actuator 12 is formed of, for example, a cylindrical piezoelectric element, and one end of the actuator 12 is fixed to a second supporting member 14c, and the other end is fixed to a second optical member 11b. The second supporting member 14c includes a cylindrical portion 14d formed at the central portion of the second supporting member 14c in radial directions thereof and extending inside the actuator 12. The lenses 10a and 10b constituting the imaging optical system 10 and the cut-off filter 34 are fixed inside the cylindrical portion 14d.

Moreover, a first supporting member 14b is disposed on a side of the optical members 11a and 11b opposite that on which the second supporting member 14c lies, and supports the first optical member 11a and the image-pickup element 13.

Figure 9:
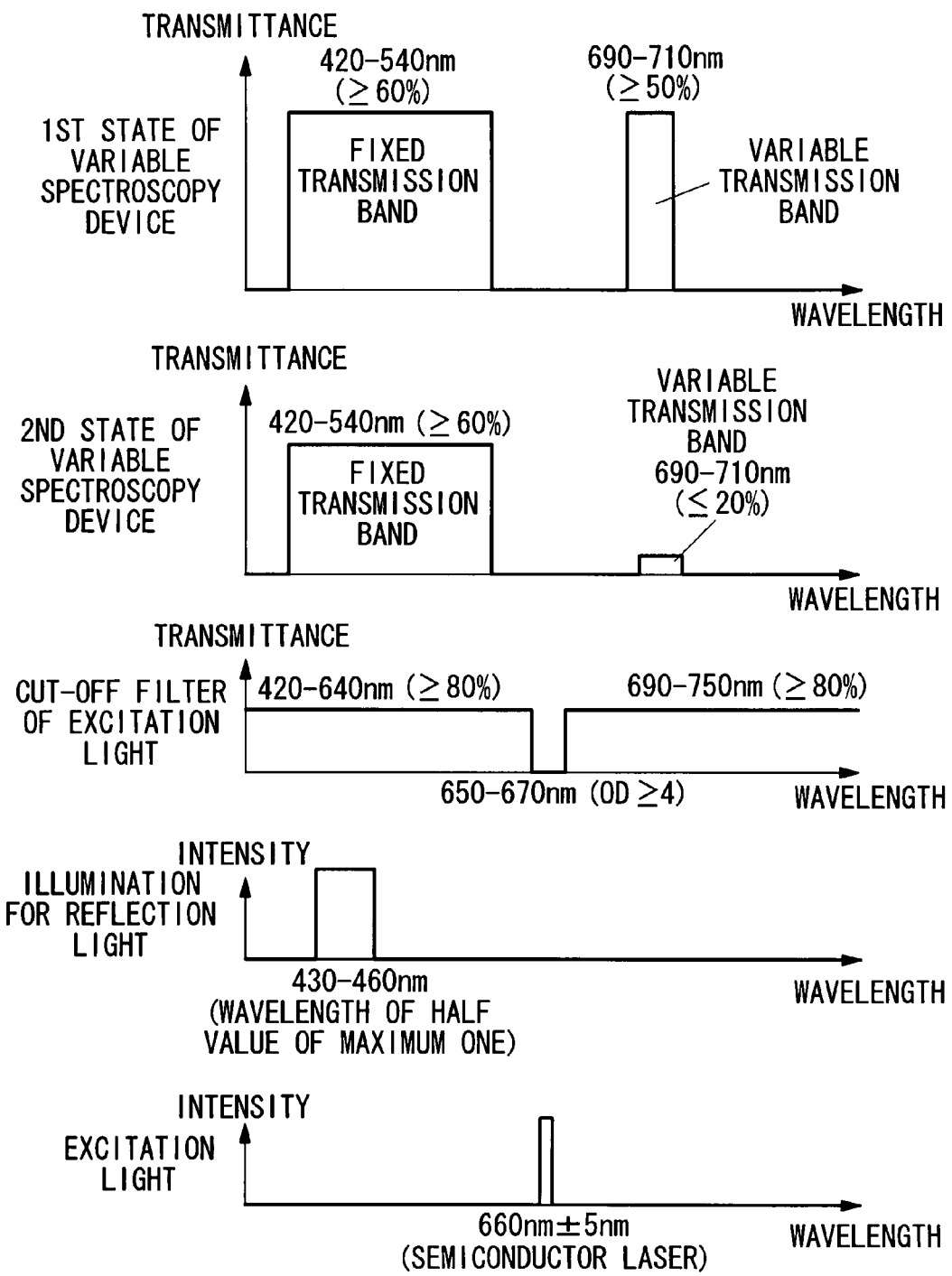
FIG. 9 illustrates transmittance characteristics of optical components constituting the image pickup unit shown in FIG. 8 and wavelength characteristics of illumination beams and excitation beams.

As shown in FIG. 9, the variable spectroscopy device 16 has transmittance characteristics including two transmission bands, one fixed transmission band and one variable transmission band. The fixed transmission band always allows passage of incoming beams regardless of the state of the variable spectroscopy device 16. Moreover, the variable transmission band changes the transmittance characteristics thereof in accordance with the state of the variable spectroscopy device 16.

In this embodiment, the variable transmission band of the variable spectroscopy device 16 is within a wavelength band (for example, from 690 to 710 nm) including the wavelength of fluorescent beams generated when a fluorescent agent is excited by excitation beams. The variable spectroscopy device 16 is switched between two states in accordance with control signals sent from the control unit 5.

In the first state, the transmittance of the variable transmission band is increased to 50% or more such that fluorescent beams transmit through the variable spectroscopy device 16.

In the second state, the transmittance of the variable transmission band is reduced to 20% or less such that fluorescent beams are blocked by the variable spectroscopy device 16. Alternatively, the second state can be defined by changing the position of the variable transmission band from that shown in the first state to another position such that fluorescent beams are blocked.

The fixed transmission band ranges from, for example, 420 to 540 nm, and the transmittance thereof is fixed to 60% or more.

Moreover, the fixed transmission band is within a wavelength band including the wavelength of reflected illumination beams. The reflected beams can transmit through the variable spectroscopy device 16 toward the image-pickup element 13 when the variable spectroscopy device 16 is either in the first state or in the second state.

Moreover, the transmittances of the cut-off filter 34 are 80% or more in a wavelength band from 420 to 640 nm, 4 or more in optical density (i.e., transmittance $1 \times 10^{-4}$ or less) in a wavelength band from 650 to 670 nm, and 80% or more in a wavelength band from 690 to 750 nm.

A second control circuit 17 for driving the image-pickup device 13 and a third control circuit 18 for controlling the variable spectroscopy device 16 are connected to the light source control circuit 9 so as to control the image-pickup element 13 and the variable spectroscopy device 16, respectively, in synchronization with switching between the illumination light source 32 and the excitation light source 33 performed by the light source control circuit 9.

Figure 10:
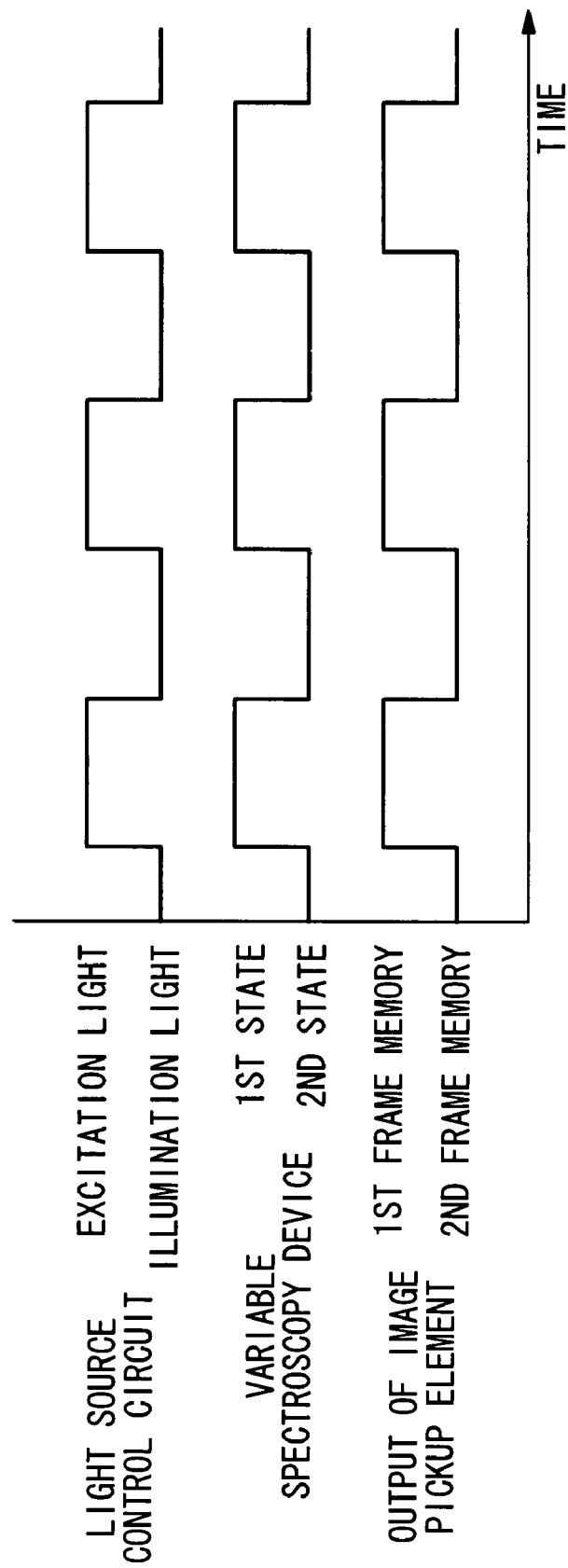
FIG. 10 is a timing chart illustrating operations of the endoscope system shown in FIG. 7.

More specifically, as shown in a timing chart in FIG. 10, when excitation beams are emitted from the excitation light source 33 in accordance with the operation of the light source control circuit 9, the third control circuit 18 drives the variable spectroscopy device 16 to be switched to the first state, and the second control circuit 17 drives the image-pickup element 13 to output the image information to a first frame-memory segment 19a. Moreover, when illumination beams are emitted from illumination light source 32, the third control circuit 18 drives the variable spectroscopy device 16 to be switched to the second state, and the second control circuit 17 drives the image-pickup element 13 to output the image information to a second frame-memory segment 19b.

Moreover, an image-processing circuit 20 receives, for example, image information on fluorescent beams generated by irradiation of excitation beams from the first frame-memory segment 19a, and outputs the information to a first channel of the display unit 6. Alternatively, the image-processing circuit 20 receives image information on reflected beams generated by irradiation of illumination beams from the second frame-memory segment 19b, and outputs the information to a second channel of the display unit 6.

Operations of the endoscope system 31 including the above-described image pickup unit 30 according to this embodiment will now be described.

In order to capture images of the observation target A in a cavity of a living body using the endoscope system 31 including the image pickup unit 30 according to this embodiment, a fluorescent agent is injected into the body, the insertion section 3 is inserted into the cavity, and is disposed such that the leading end 3a of the insertion section 3 faces the observation target A in the cavity. In this arrangement, the light source unit 4 and the control unit 5 are operated such that the illumination light source 32 and the excitation light source 33 alternately emit illumination beams and excitation beams, respectively, in accordance with the operation of the light source control circuit 9.

The excitation beams and the illumination beams generated at the light source unit 4 are transmitted to the leading end 3a of the insertion section 3 via the light guide 7, and emitted from the leading end 3a of the insertion section 3 to the observation target A.

When the excitation beams are incident on the observation target A, the fluorescent agent transmitting the observation target A is excited so as to generate fluorescent beams. The fluorescent beams generated at the observation target A are collected by the imaging optical system 10 of the image pickup unit 30, and enter the variable spectroscopy device 16 via the cut-off filter 34.

Since the variable spectroscopy device 16 is switched to the first state in accordance with the operation of the second control circuit 17 in synchronization with the operation of the excitation light source 33, transmittance of fluorescent beams is increased, and the incident fluorescent beams can transmit through the variable spectroscopy device 16. In this case, part of the excitation beams incident on the observation target A is reflected from the observation target A, and directed to the image pickup unit 30 together with the fluorescent beams. However, the excitation beams are blocked from entering the image-pickup element 13 by the cut-off filter 34 provided for the image pickup unit 30.

The fluorescent beams transmitting through the variable spectroscopy device 16 then enter the image-pickup element 13 such that image information on the fluorescent beams is acquired. The acquired image information on the fluorescent beams is retained in the first frame-memory segment 19a, output by the image-processing circuit 20 to the first channel of the display unit 6, and displayed on the display unit 6.

On the other hand, when illumination beams are incident on the observation target A, the illumination beams are reflected from the surface of the observation target A, and collected by the imaging optical system 10 so as to enter the variable spectroscopy device 16 via the cut-off filter 34. Since the wavelength band of the reflected illumination beams is within the fixed transmission band of the variable spectroscopy device 16, all the reflected beams incident on the variable spectroscopy device 16 can transmit through the variable spectroscopy device 16.

The reflected beams transmitting through the variable spectroscopy device 16 are incident on the image-pickup element 13 such that image information on the reflected beams is acquired. The acquired image information on the reflected beams is retained in the second frame-memory segment 19b, output by the image-processing circuit 20 to the second channel of the display unit 6, and displayed on the display unit 6.

In this case, transmittance of fluorescent beams is reduced since the variable spectroscopy device 16 is switched to the second state in accordance with the operation of the third control circuit 18 in synchronization with the operation of the illumination light source 32. Therefore, fluorescent beams are blocked from entering the image-pickup element 13. As a result, only the reflected beams are captured by the image-pickup element 13.

In accordance with the endoscope system 31 including the image pickup unit 30 according to this embodiment, images of fluorescent beams and images of reflected beams can be provided for a user.

In accordance with the image pickup unit 30 according to this embodiment, the lenses 10a and 10b constituting the imaging optical system 10 and the cut-off filter 34 are disposed inside the cylindrical actuator 12. Therefore, the second optical member 11b supported by the actuator 12 and the second lens 10b constituting the imaging optical system 10 can be disposed close to each other. Thus, the numerical aperture for the light beams that enter the second lens 10b can be ensured without increasing the size of the second lens 10b even when convergent beams pass through the variable spectroscopy device 16. This leads to a bright lens system that can be advantageously used for observation of fluorescent beams, which are, in general, weak.

Figure 11:
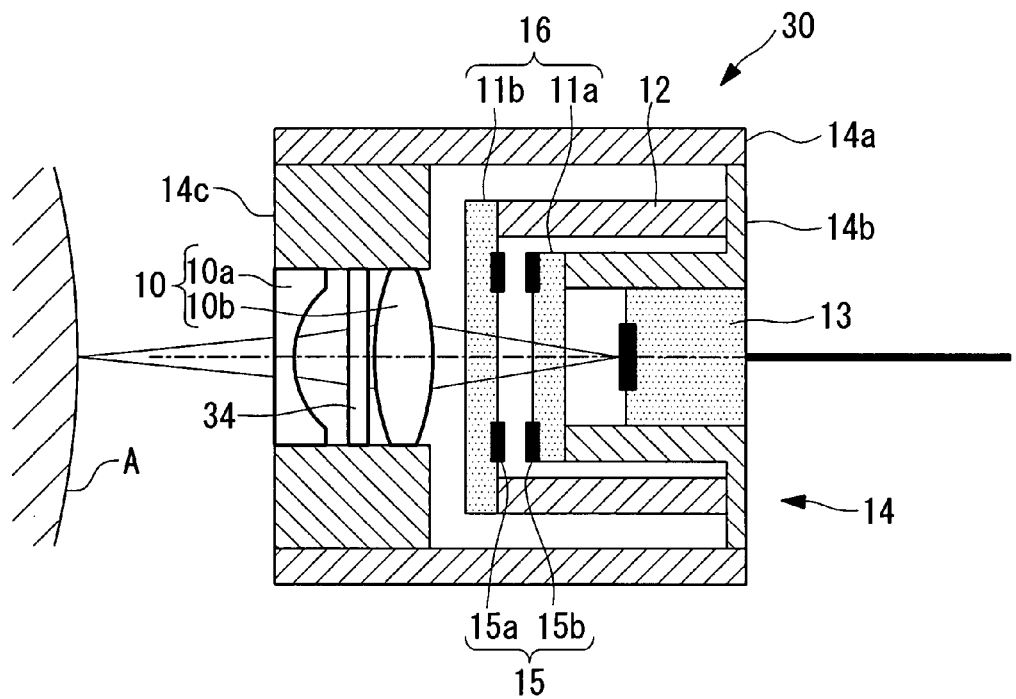
FIG. 11 is a schematic longitudinal sectional view illustrating a modification of the image pickup unit shown in FIG. 8.

In this embodiment, the optical members 11a and 11b constituting the variable spectroscopy device 16 are supported by the separate supporting members 14b and 14c, respectively. Alternatively, as shown in FIG. 11, the first optical member 11a can be supported at the end of the cylindrical portion 14d of the first supporting member 14b that supports the second optical member 11b via the actuator 12. As a result, the length of the actuator 12 in the axial direction thereof can be increased so as to achieve high driving resolution by ensuring the moving distance of the actuator 12.

Figure 12:
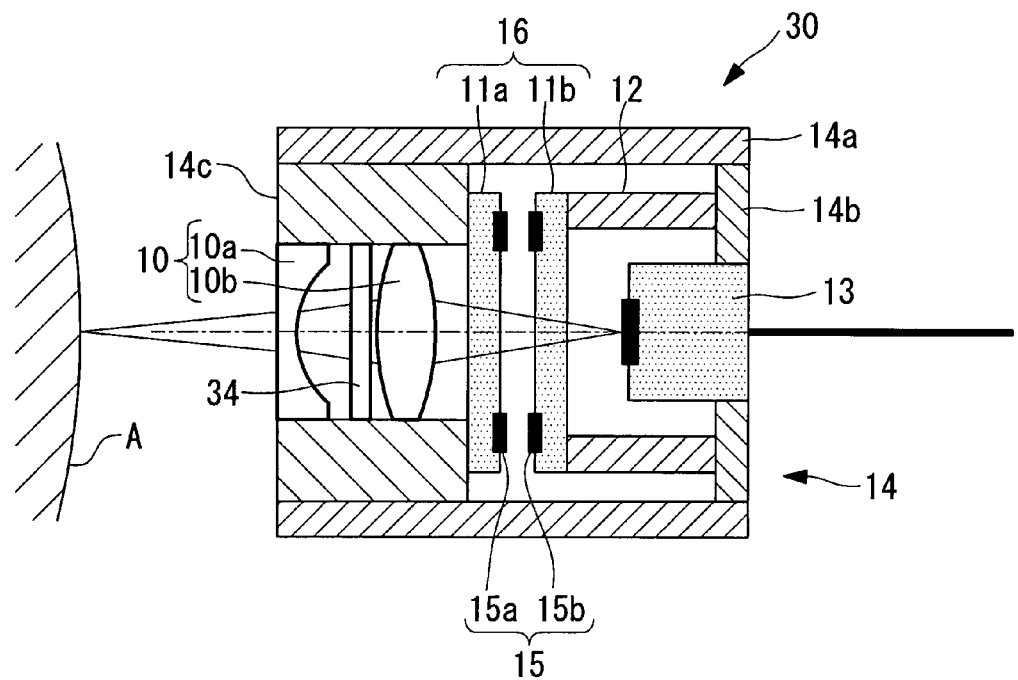
FIG. 12 is a schematic longitudinal sectional view illustrating another modification of the image pickup unit shown in FIG. 8.
Figure 13:
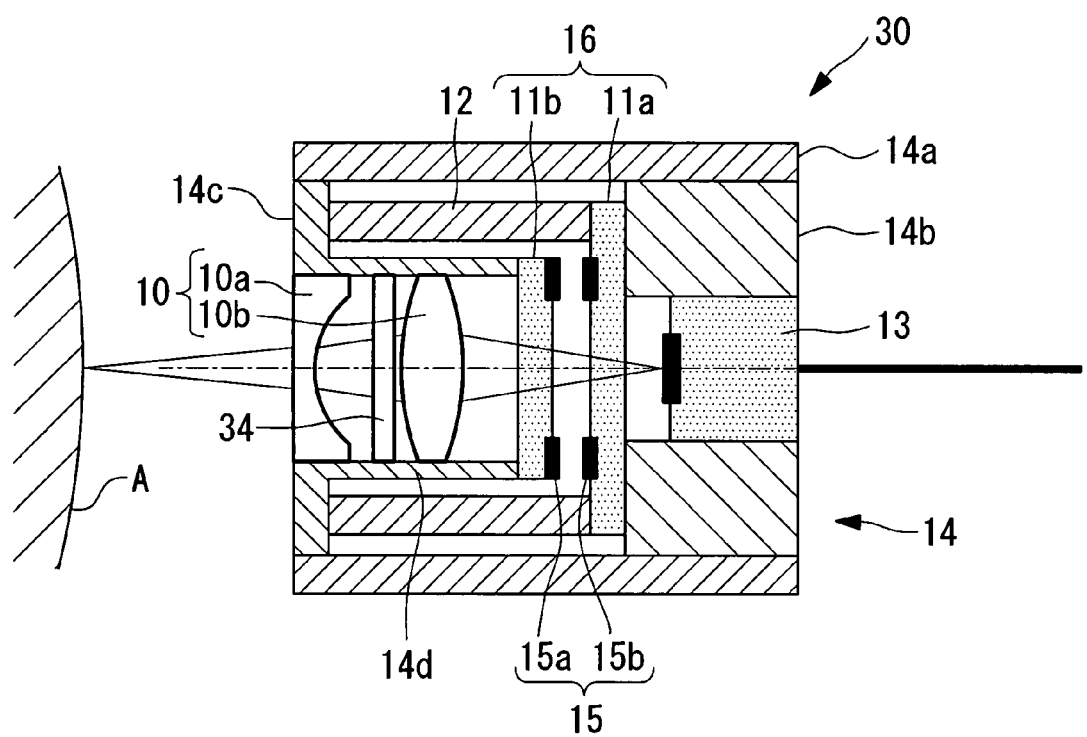
FIG. 13 is a schematic longitudinal sectional view illustrating yet another modification of the image pickup unit shown in FIG. 8.

Moreover, the size of the second lens 10b is reduced by disposing the imaging optical system 10 inside the cylindrical actuator 12 such that the lenses 10a and 10b and the second optical member 11b are disposed close to each other. However, the same effect can be achieved by disposing the image-pickup element 13 inside the actuator 12 as shown in FIG. 12. Moreover, as shown in FIG. 13, the imaging optical system 10 can be disposed inside the cylindrical portion 14d formed on the second supporting member 14c that supports the first optical member 11a via the actuator 12, and the second optical member 11b can be disposed at the end of the cylindrical portion 14d such that the moving distance of the actuator 12 is ensured.

Moreover, light beams passing through the optical members 11a and 11b are convergent beams in the description above. However, the optical members 11a and 11b can be disposed at positions where light beams diverge.

Moreover, the actuator 12 is not limited to a piezoelectric element, and can be, for example, a cylindrical member composed of a material having a high thermal conductivity such as copper and having a heating element disposed on the side surface thereof so as to use the thermal expansion thereof. As a result, hysteresis, which is sometimes observed in piezoelectric elements, can be regulated, and the actuator can be easily controlled with high accuracy.

Next, an optical apparatus 40 for capturing spectral images according to a third embodiment of the present invention and an endoscope system 41 including the optical apparatus 40 will be described with reference to FIGS. 14 and 15.

In the description of this embodiment, the same reference numerals are used for components common to those in the endoscope system 2 according to the first embodiment, and the description thereof will be omitted.

The endoscope system 41 in this embodiment differs from the endoscope system 2 in the first embodiment in that the endoscope system 41 uses the optical apparatus 40 as a part of a light source unit 42 whereas the endoscope system 2 uses the optical apparatus as the image pickup unit 1 in the first embodiment.

Figure 14:
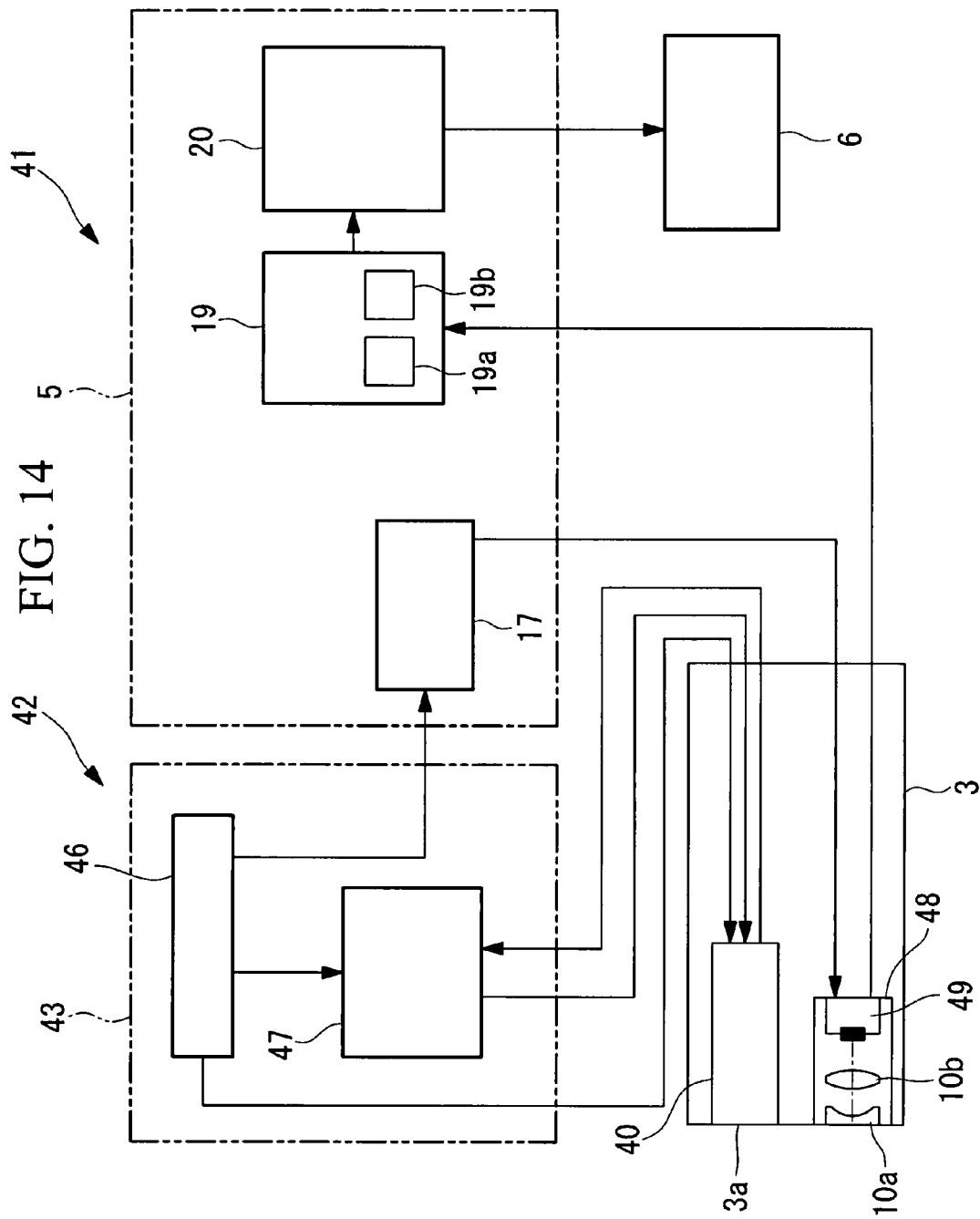
FIG. 14 is a block diagram illustrating the structure of an endoscope system including a light source unit according to a third embodiment of the present invention.

That is, as shown in FIG. 14, the light source unit 42 includes a light source section (optical apparatus) 40 disposed at the leading end 3a of an insertion section 3 and a control section 43 that controls the light source section 40 disposed outside the optical apparatus 40.

Figure 15:
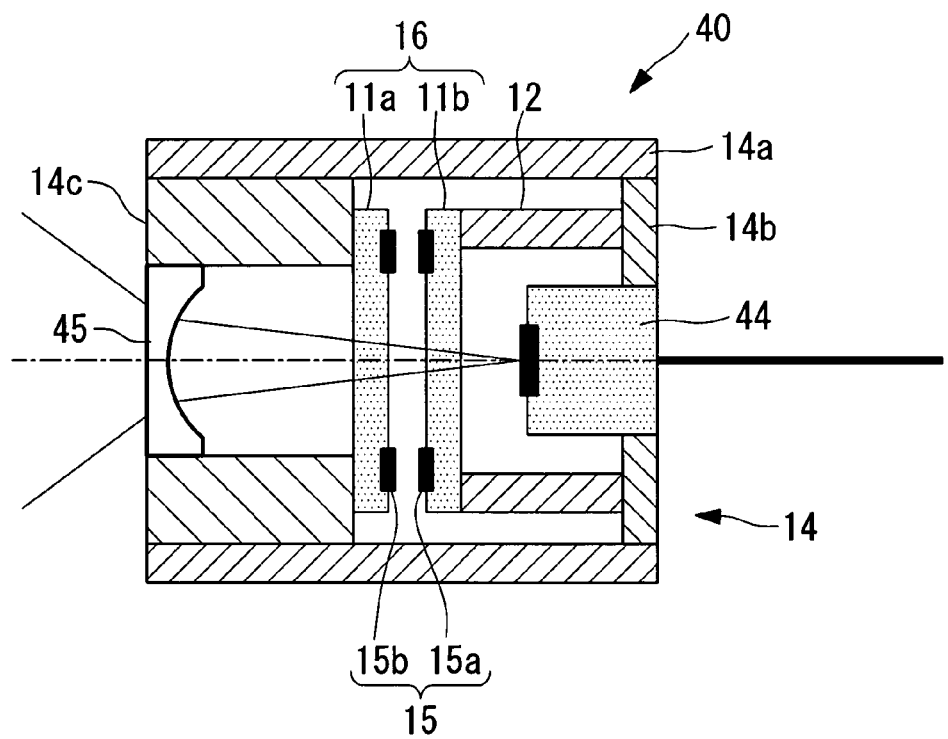
FIG. 15 is a schematic longitudinal sectional view illustrating the light source unit according to the third embodiment of the present invention.

As shown in FIG. 15, the light source section 40 includes a white light emitting diode (LED; photoelectric conversion element) 44 that emits white beams, a variable spectroscopy device 16 including two optical members 11a and 11b, an actuator 12, a lens 45 that diffuses the white beams emitted from the white LED 44, and a frame member 14 that fixes these components.

The actuator 12 is formed of, for example, a cylindrical piezoelectric element, and one end of the actuator 12 is fixed to a first supporting member 14b, and the other end is fixed to the second optical member 11b. In this embodiment, the white LED 44 is disposed inside the actuator 12.

Moreover, a second supporting member 14c is disposed on a side of the optical members 11a and 11b opposite that on which the first supporting member 14b lies, and supports the first optical member 11a.

The control section 43 includes a light source control circuit 46 that controls on-off operations of the white LED 44 and a third control circuit 47 that switches transmission wavelength bands of the variable spectroscopy device 16.

An image pickup unit 48 in this embodiment includes lenses 10a and 10b that are fixed to the leading end 3a of the insertion section 3 and an image-pickup element 49 that captures light beams reflected from an observation target A and collected by the lenses 10a and 10b.

In accordance with the above-described light source section 40 according to this embodiment, spectral images can be captured by switching the transmission wavelength bands of the variable spectroscopy device 16.

Since the white LED 44 is disposed inside the actuator 12 in this case, the white LED 44 can be disposed close to the first optical member 11a while a long moving distance of the actuator 12 is ensured.

As a result, the total length of the light source unit can be reduced, and the numerical aperture for the illumination beams that pass through the lens 45 can be ensured without increasing the size of the lens 45 even when divergent illumination beams pass through the optical members 11a and 11b. This leads to bright illumination.

Moreover, in the case of a surface illuminant having a plurality of white LEDs 44, the external diameter of the lens 45 required when the surface illuminant is separated from the lens 45 is increased as compared with the case of a point light source. In such a case, in accordance with the light source section 40 according to this embodiment, the total length of the light source section 40 can be advantageously reduced without increasing the size of the lens 45.

In this embodiment, the white LED 44 is used as a light source, and the number in which the white LED 44 is provided can be one, or two or more. Moreover, a combination of the white LED 44 and a diffusing plate (not shown) for increasing the area of the light source or a lamp (not shown) can be used as a light source. Moreover, a semiconductor laser capable of multiwavelength excitation, a superluminescent diode, and the like can also be used as a light source.

Figure 16:
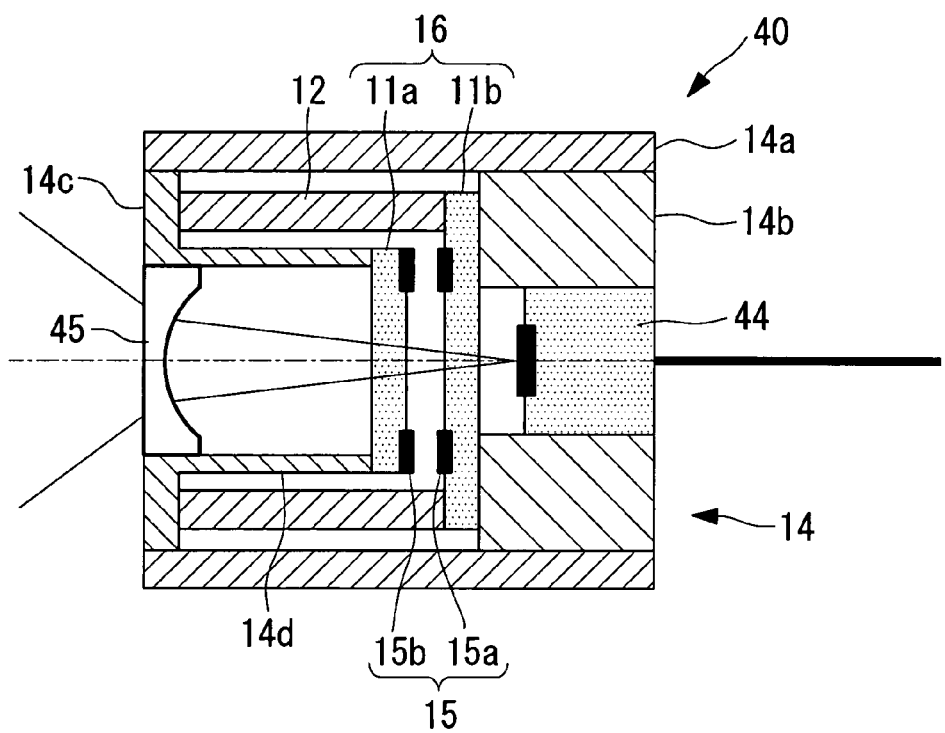
FIG. 16 is a schematic longitudinal sectional view illustrating a modification of the light source unit shown in FIG. 15.

Moreover, as shown in FIG. 16, the actuator 12 can be disposed between the second supporting member 14c and the second optical member 11b, and the first optical member 11a and the lens 45 can be disposed inside the actuator 12 instead of disposing the white LED 44 inside the cylindrical actuator 12 that is disposed between the first supporting member 14b and the second supporting member 14c.

Figure 17:
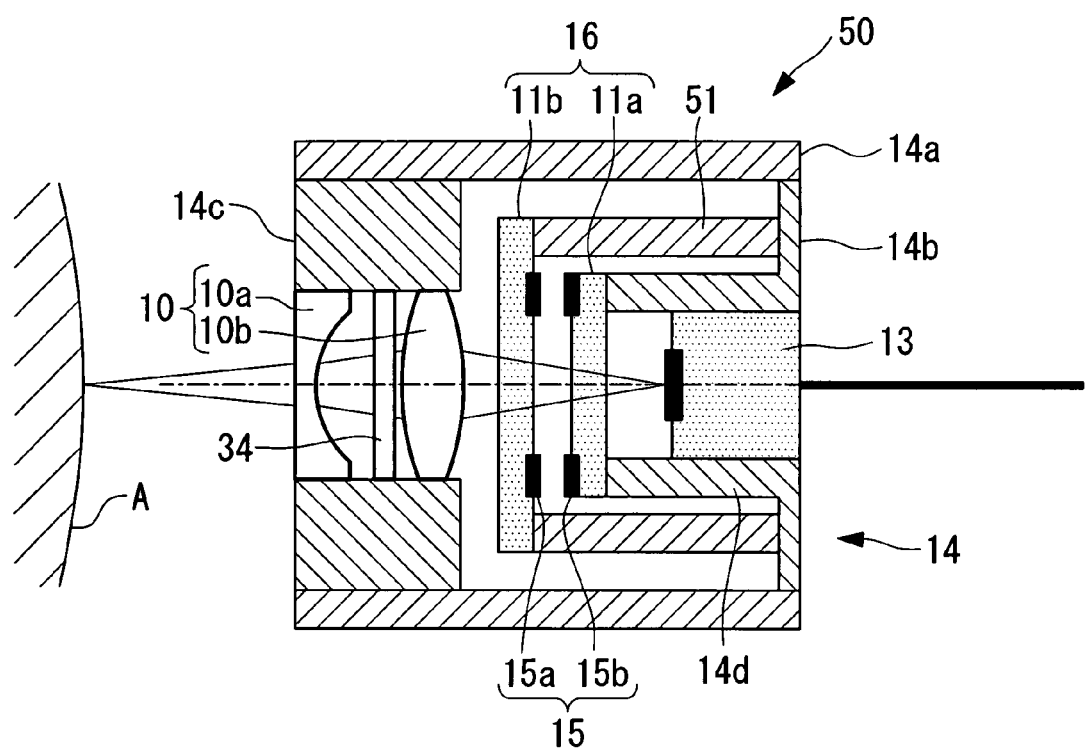
FIG. 17 is a schematic longitudinal sectional view illustrating an image pickup unit according to a fourth embodiment of the present invention.

Next, an optical apparatus 50 for capturing spectral images according to a fourth embodiment of the present invention will be described with reference to FIG. 17.

The optical apparatus 50 according to this embodiment is the same image pickup unit as that shown in FIG. 11 in accordance with the optical apparatus 30 according to the second embodiment. However, the structure of the actuator differs from that in the second embodiment. Therefore, the same reference numerals are used for components common to those in the optical apparatus 30 according to the second embodiment shown in FIG. 11, and the description thereof will be omitted.

In the image pickup unit (optical apparatus) 50 according to this embodiment, a plurality of (for example, four) rod-shaped actuators 51 are disposed around the optical axis of optical members 11a and 11b and an image-pickup element 13 with a space therebetween in the circumferential direction unlike the cylindrical actuator 12 in the second embodiment. Moreover, in this embodiment, sensor electrodes 15a and 15b of a capacitive sensor 15 are also divided into the same number of the actuators 51 (for example, four), and disposed at positions corresponding to the actuators 51 with a space therebetween in the circumferential direction.

In accordance with the above-described image pickup unit 50 according to this embodiment, the sensor electrodes 15a and 15b and the actuators 51 are divided in the circumferential direction, and arranged so as to be separated from each other. Therefore, the relative inclination of the optical members 11a and 11b can be detected by the independent and separate sensor electrodes 15a and 15b, and the second optical member 11b can be moved by the independent actuators 51 such that the inclination is corrected.

In general, intensity of fluorescent beams obtained during fluorescence observation is weak. Therefore, the transmission efficiency of the optical system is extremely important. The transmission efficiency of the optical members 11a and 11b is high when the optical members 11a and 11b are accurately covered with reflective coatings and are disposed parallel to each other. However, when the degree of parallelization is reduced, the transmission efficiency is rapidly reduced. In accordance with the image pickup unit 50 according to this embodiment, the moving distance of the second optical member 11b can be ensured, and at the same time, the inclination of the second optical member 11b can also be adjusted. Thus, the transmission efficiency can be improved, and bright fluorescent images can be captured.

What is claimed is:

1. An optical apparatus for capturing spectral images, comprising:
   a variable spectroscopy device having a first optical member and a second optical member that face each other and have a space therebetween, wherein the spectral characteristics of the variable spectroscopy device are changed in accordance with changes in the relative positions of these optical members;
   a frame member that fixes the first optical member in place;
   a driving section disposed between the frame member and the second optical member, and transferring the second optical member with respect to the frame member in accordance with driving signals input to the driving section; and
   an optical element that deflects or disperses light beams passing through the variable spectroscopy device or a photoelectric conversion element that conducts photoelectric conversion, wherein
   the optical element or the photoelectric conversion element is supported by the frame member.

2. The optical apparatus according to claim 1, wherein the optical apparatus is used for capturing spectral images of body tissue.

3. The optical apparatus according to claim 1, wherein the optical apparatus is used for capturing spectral images of tissue inside a cavity of a living body.

4. The optical apparatus according to claim 1, wherein at least part of the driving section, and part of the optical element or part of the photoelectric conversion element are overlapped with each other in a direction of the optical axis of the optical apparatus.

5. The optical apparatus according to claim 1, wherein the optical element is a lens or a filter.

6. The optical apparatus according to claim 1, wherein the photoelectric conversion element converts incident light into electrical energy, or converts input electrical energy into light.

7. The optical apparatus according to claim 1, wherein the driving section is arranged to be on both sides of the optical axis of the optical apparatus.

8. The optical apparatus according to claim 1, wherein the driving section transfers the second optical member in the direction of the optical axis of the optical apparatus.

9. The optical apparatus according to claim 1, wherein the first optical member is disposed between the second optical member and a position where the driving section is supported by the frame member.

10. The optical apparatus according to claim 1, wherein the second optical member is disposed between the first optical member and a position where the driving section is supported by the frame member.

11. The optical apparatus according to claim 1, wherein
   the photoelectric conversion element is a light-receiving element; and
   the optical element focuses light beams passing through the variable spectroscopy device on the light-receiving element.

12. The optical apparatus according to claim 11, wherein the light beams passing through the variable spectroscopy device are non-collimated beams.

13. The optical apparatus according to claim 12, wherein the optical element has a refractive power to the light beams passing through the variable spectroscopy device.

14. The optical apparatus according to claim 1, wherein
   the photoelectric conversion element is a light source; and
   the optical element projects light beams passing through the variable spectroscopy device onto an observation target.

15. The optical apparatus according to claim 14, wherein the light source is a surface illuminant.

16. The optical apparatus according to claim 14, wherein the light beams passing through the variable spectroscopy device are non-collimated beams.

17. The optical apparatus according to claim 16, wherein the optical element has a refractive power to the light beams passing through the variable spectroscopy device.

18. The optical apparatus according to claim 1, wherein
   the frame member is cylindrical; and
   the variable spectroscopy device, the driving section, and the optical element or the photoelectric conversion element are disposed inside the frame member.

19. The optical apparatus according to claim 1, wherein the driving section changes the size of the space between the first optical member and the second optical member.

20. The optical apparatus according to claim 19, further comprising:
   a gap-detecting section that detects the size of the space between the first optical member and the second optical member.

21. An endoscope system comprising:
   an insertion section configured to be inserted into a cavity of a living body;
   an optical apparatus according to claim 1 disposed inside the insertion section;
   a light source that emits a plurality of types of light beams;
   a control section that controls the optical apparatus and the light source; and
   a display section that displays images captured by the optical apparatus.

22. An optical apparatus for capturing spectral images, comprising:
   a variable spectroscopy means having a first optical member and a second optical member that face each other and have a space therebetween, wherein the spectral characteristics of the variable spectroscopy means are changed in accordance with changes in the relative positions of these optical members;
   a fixing means that fixes the first optical member in place;
   a driving means disposed between the fixing means and the second optical member, and transferring the second optical member with respect to the fixing means in accordance with driving signals input to the driving means; and
   an optical means that deflects or disperses light beams passing through the variable spectroscopy means or a photoelectric-conversion means that conducts photoelectric conversion, wherein
   the optical means or the photoelectric-conversion means is supported by the fixing means.

23. An endoscope system comprising:
   an insertion section configured to be inserted into a cavity of a living body;
   an optical apparatus according to claim 21 disposed inside the insertion section;

a light-generating means that emits a plurality of types of light beams;

a controlling means that controls the optical apparatus and the light-generating means; and a displaying means that displays images captured by the optical apparatus.

* * * * *